(12) United States Patent
Rao

(10) Patent No.: US 8,554,195 B2
(45) Date of Patent: Oct. 8, 2013

(54) HEALTH MANAGEMENT SYSTEM FOR GROUP INTERACTIONS BETWEEN PATIENTS AND HEALTHCARE PRACTITIONERS

(76) Inventor: Bindu Rama Rao, Laguna Niguel, CA (US)

( * ) Notice: Subject to any disclaimer, the term of this patent is extended or adjusted under 35 U.S.C. 154(b) by 0 days.

(21) Appl. No.: 13/281,134

(22) Filed: Oct. 25, 2011

(65) Prior Publication Data
US 2012/0072234 A1 Mar. 22, 2012

Related U.S. Application Data

(63) Continuation-in-part of application No. 12/221,876, filed on Aug. 6, 2008.

(51) Int. Cl.
*H04M 3/00* (2006.01)

(52) U.S. Cl.
USPC ..... 455/420; 455/456.3; 455/419; 455/422.1; 455/552.1; 455/550.1; 709/203; 709/217; 709/224

(58) Field of Classification Search
USPC ..... 455/550.1, 556.2, 456.3, 456.6, 418–419, 455/412.1, 413.3, 466, 420, 422.1, 552.1, 455/456.1, 412.2; 705/2–3; 709/224, 203, 709/217
See application file for complete search history.

(56) References Cited

U.S. PATENT DOCUMENTS

| | | | |
|---|---|---|---|
| 6,968,375 B1 * | 11/2005 | Brown | 709/224 |
| 2006/0212316 A1 * | 9/2006 | Jackson et al. | 705/3 |
| 2009/0132286 A1 * | 5/2009 | Blaquier | 705/3 |

* cited by examiner

*Primary Examiner* — Vladimir Magloire
*Assistant Examiner* — Babar Sarwar

(57) ABSTRACT

A health management system for managing the healthcare data of patients, managing interactions with patients, doctors and insurance companies, and managing group messaging and data access from mobile phones of patients and doctors. The health management system facilitates interaction with a plurality of patients. It comprises a patient group management server that is communicatively coupled to a plurality of mobile devices of patients. The patient group management server in turn comprises a message interaction module, a questionnaire distribution and feedback collection module, a remote patient premises data collection module, a coaching distribution module and a content distribution service module. The patient group management server enables communication to each other of an inquiry, a response message, a coaching and guided activity, a questionnaire and relevant reference content by members of the patient group.

20 Claims, 3 Drawing Sheets

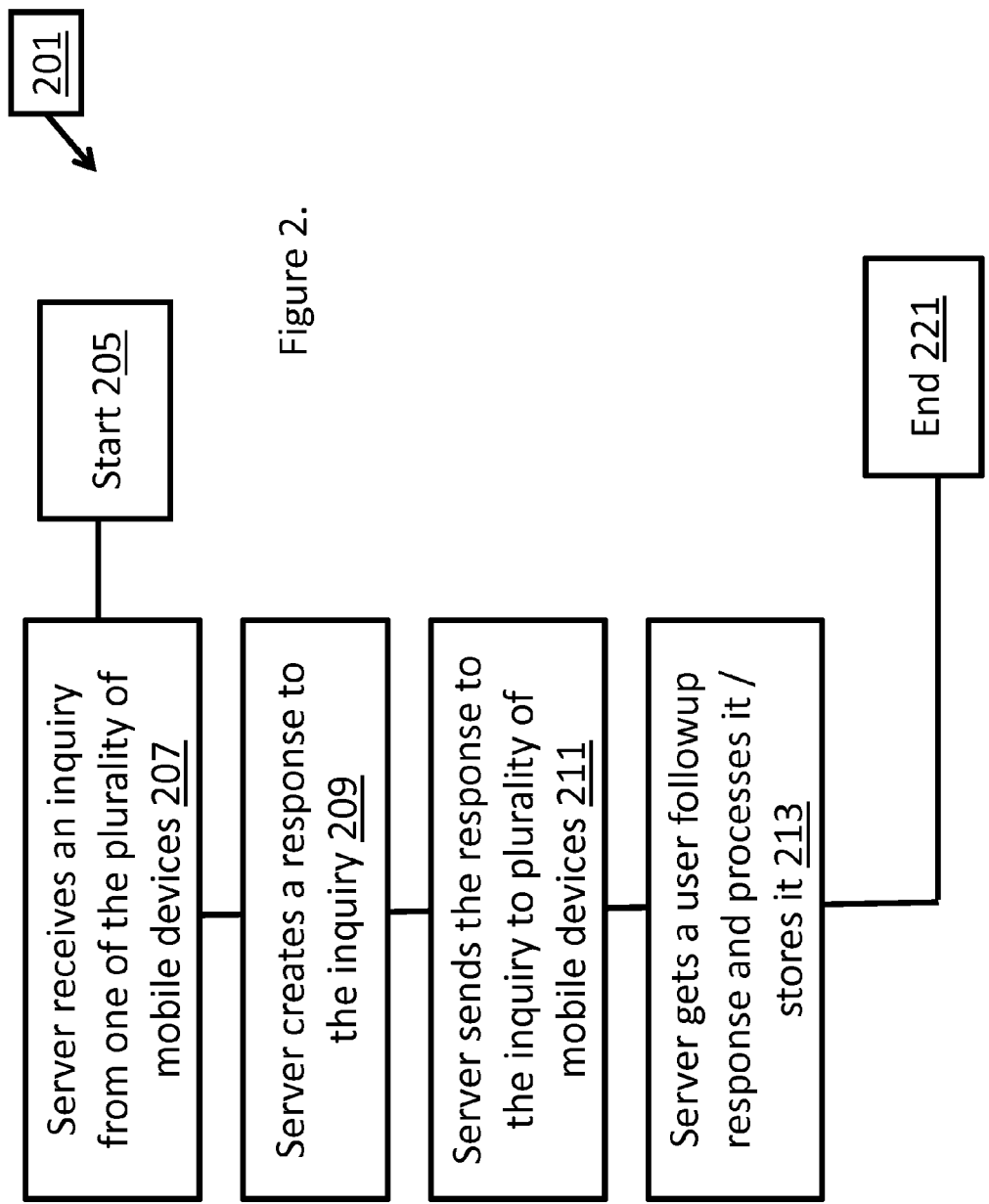

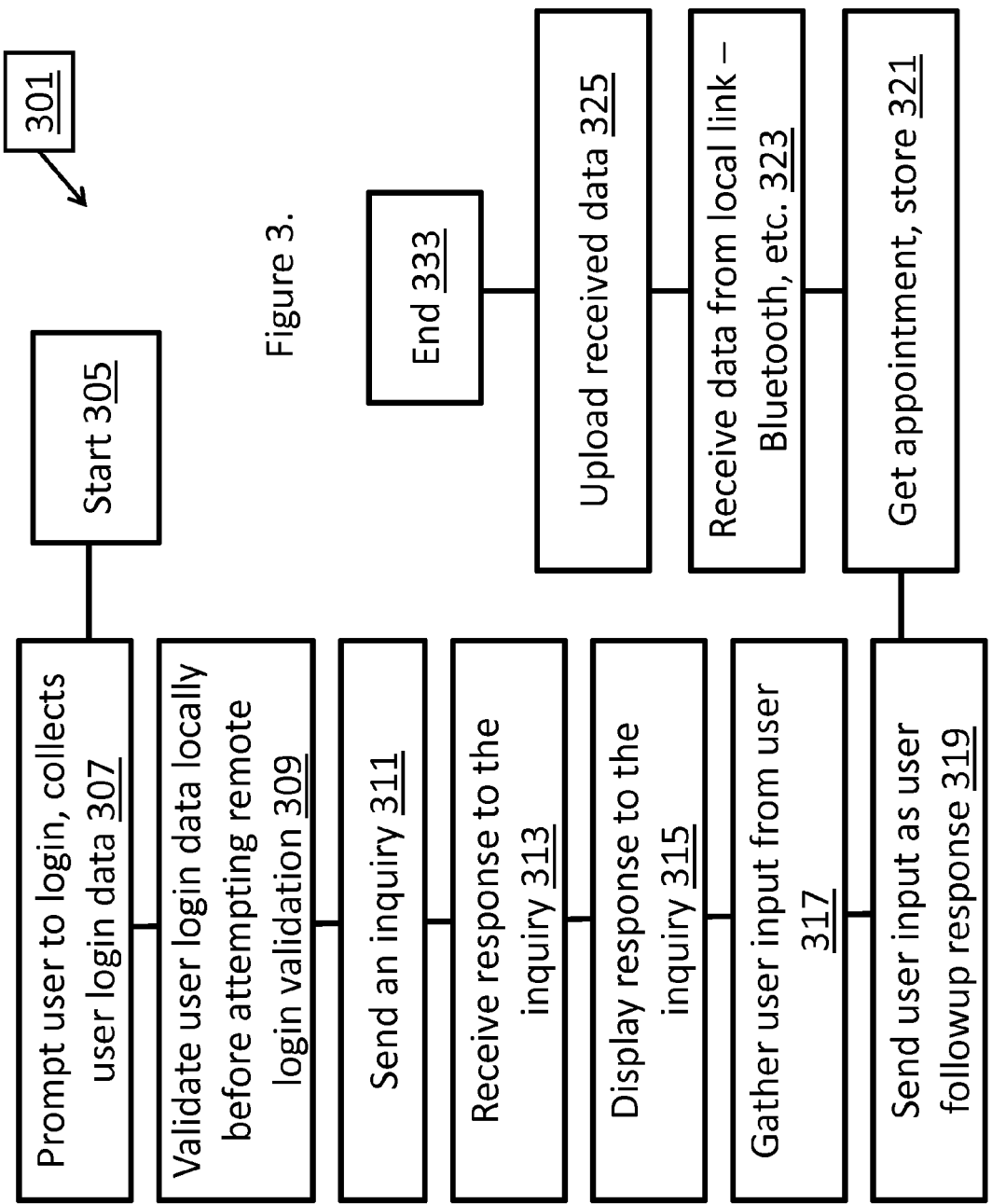

HEALTH MANAGEMENT SYSTEM FOR GROUP INTERACTIONS BETWEEN PATIENTS AND HEALTHCARE PRACTITIONERS

CROSS REFERENCES TO RELATED APPLICATIONS

The present patent application is a continuation-in-parts of, is a based on, and makes reference to U.S. non-provisional patent Ser. No. 12/221,876, entitled "Mobile device for access to agricultural services by non-literate and semi-literate users", filed on Aug. 6, 2008. The complete subject matter of the above-referenced United States Patent Application is hereby incorporated herein by reference, in its entirety.

The present patent application is based on and makes reference to United States non-provisional patent entitled QUESTIONNAIRE SERVER CAPABLE OF PROVIDING QUESTIONNAIRES BASED ON DEVICE CAPABILITIES, Ser. No. 11/807,672, filed May 30, 2007, which in turn is based on a U.S. provisional patent application, Ser. No. 60/858,546, filed on Nov. 13, 2006. The complete subject matter of this referenced United States Patent Application is hereby incorporated herein by reference, in its entirety.

The present patent application is based on and makes reference to United States non-provisional patent entitled MOBILE WEB SYSTEM PROVIDING INTERCHANGABLE SERVICE WITH A MOBILE DEVICE, Ser. No. 12/011,238, filed Jan. 25, 2008, which in turn is based on U.S. non-provisional patent application Ser. No. 11/807,670, entitled "MOBILE DEVICE AND SERVER CAPABLE OF SUPPORTING ADHOC QUESTIONNAIRES", filed on May 30, 2007. The complete subject matter of the above-referenced U.S. patent application is hereby incorporated herein by reference, in its entirety.

BACKGROUND

1. Technical Field

This present invention relates generally to mobile services and more specifically to employing a mobile phone for interactions with a health care system.

2. Related Art

In the last few years, Internet technologies have proliferated and millions of people use the Internet for business and for personal activities. In addition, social networks have taken off wherein a number of people can communicate with each other using Internet based systems such as Facebook. However, much of these technologies has not made its way to rural communities across the world, and has had limited impact on their lives.

There are several unmet needs for users who live in small rural communities, and some of these are being met by means of mobile phones. There is need for new solutions that can be managed, with proper control over who can conduct specific activities, especially for healthcare related issues and interactions with doctors and health care providers. Ordinarily, quite a few people make frequent visits to doctors, and let the doctors treat them for various ailments. However, interactions between patients and doctors are limited to visiting a clinic or talking to the doctor over a phone. Frequent visits to a doctor's office or a clinic to obtain information on patient care, medications etc. are not only time consuming but also expensive. However, there are no easy ways to avoid them for elders, senior citizens and those with ailments.

Mobile devices are becoming ubiquitous. People in urban areas carry them and so do people living in rural communities. Most people working in remote locations use mobile phones to stay in touch with their family, customers and take phone calls throughout the day. However, the use by ordinary people of their mobile phones to avail of healthcare services is non-existent/rare.

Urban-oriented hospitals and doctor's offices in the developing world, such as India, perceive business prospects in shifting focus to the rural sector. The rural Indian market, for example, a hitherto much neglected one, is now emerging as a large pool of high net worth individuals, traders, entrepreneurs, processing industries, marketing and warehousing agencies, market intermediaries, professionals, educational institutions, plantations and so on provides a wide range of business avenues and market for these institutions to diversify the risks and also seek growth.

Despite decades of effort and experimentation in rural healthcare solutions, the organised healthcare sector is still not able to meet the healthcare gap in the rural sector. It took time for hospitals and doctor's offices to realise the potential of the rural markets. Lack of infrastructure in the rural areas and the focus in the urban sector were some of the reasons. In view of this, there is great need for technology to provide support to the rural populace via an easy mode of access to healthcare services, medical information, and other related facilities.

One of the main problems in rural places (villages, small towns, etc.) in the world is the lack of primary care clinics in proximity to the rural communities. People with meager incomes cannot afford to travel frequently to big cities seeking medical care or information.

Accordingly, the present invention addresses the need for rural people to seek medical information, medical services, share information with other patients, interact with their physicians, etc. despite the lack of traditional healthcare facilities such as clinics and hospitals nearby. The present invention enables easy & secure access to medical information, doctor's, expert opinion, without the need for any additional infrastructure costs to the users and the healthcare organizations.

In view of the foregoing considerations, it is clear that there is a need for an improved system and method for providing interactions between doctors and their patients, between healthcare companies and their customers, between people in rural communities, where there are very few healthcare facilities, etc.

Further limitations and disadvantages of conventional and traditional approaches will become apparent to one of ordinary skill in the art through comparison of such systems with the present invention.

BRIEF SUMMARY OF THE INVENTION

The present invention is directed to apparatus and methods of operation that are further described in the following Brief Description of the Drawings, the Detailed Description of the Invention, and the claims. Other features and advantages of the present invention will become apparent from the following detailed description of the invention made with reference to the accompanying drawings.

BRIEF DESCRIPTION OF THE DRAWINGS

FIG. 2 is a flow chart of an exemplary operation of the patient group management server of the health management system.

FIG. 3 is a flow chart of an exemplary interaction by a mobile client in a mobile device and the patient group management server in the health management system.

DETAILED DESCRIPTION OF THE DRAWINGS

Figure 1:
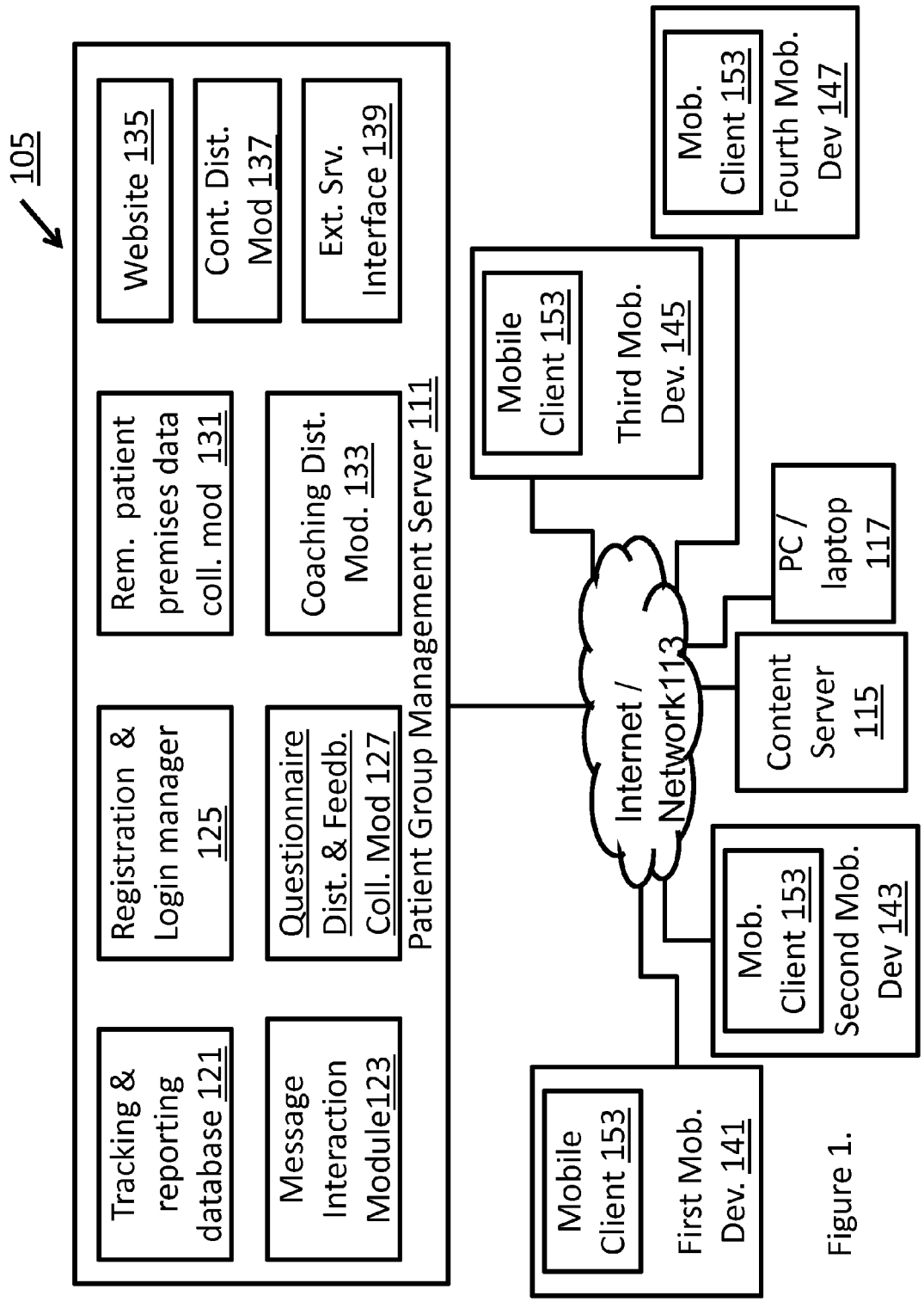
FIG. 1 is a perspective block diagram of a health management system for managing the healthcare data of patients, managing interactions with patients, doctors and insurance companies, and managing group messaging and data access from mobile phones of patients and doctors.

The present invention describes a health management system for group interactions between patients and healthcare practitioners. The patients and healthcare practitioners can use their mobile phones or laptop/computers to interact with each other, access data from remote places, send messages to patient groups, etc.

FIG. 1. is a perspective block diagram of a health management system 105 for managing the healthcare data of patients, managing interactions with patients, doctors and insurance companies, and managing group messaging and data access from mobile phones of patients and doctors. The health management system 105 facilitates interaction with a plurality of patients, It comprises a patient group management server 111 that is communicatively coupled to a plurality of mobile devices 141, 143, 145, 147 of patients and medical practitioners. The patient group management server 111 in turn comprises a message interaction module 123, a questionnaire distribution and feedback collection module 127, a remote patient premises data collection module 131, a coaching distribution module 133 and a content distribution module 137. The mobile devices 141, 143, 145, 147 interact with the patient group management server 111 over Internet/Network 113. A registration & login manager 125 in the patient group management server 111 facilitates registration of users, creating a profile optionally by users, and validation of user login name and password during remote access or access through a website 135 provided by the patient group management server 111. A tracking & reporting database 121 is used to track what inquiries have been made by individual patients and other users, if any responses have been provided or if responses are due, details of messages created, questionnaires created, references to new content and existing content, etc. The tracking & reporting database 121 is used to store groups information, group memberships, user profiles, messages received, etc. A content server 115 provides additional content to patients and others who are members/subscribers to various services provided by the health management system 105.

The message interaction module 123 facilitates creation of new messages, retrieval of new messages, forwarding of messages, gathering responses to messages, distribution of messages to a whole group, collating responses for a message, etc. wherein the messages are created, and retrieved using mobile devices 141, 143, 145, 147 or the PC/laptop 117 (which has a browser and accesses the website 135). The questionnaire distribution and feedback collection module 127 facilitates distribution of questionnaires and collection of feedback and responses from those questionnaires. It facilitates generating a spreadsheet of those responses, answers received for a question, emailing the spreadsheet of responses, etc. The remote patient premises data collection module 131 facilitates retrieval of patient data from a patient premises medical equipment via a mobile device 141, upload of such, storage and sharing of patient data at the patient group management server 111, processing of patient data, and securely forwarding patient data to authorized external server via an external server interface 139.

The coaching distribution module 133 facilitates creation of guided activities and distribution of guided activities. For example video guided activities and audio guided activities can be created, stored and distributed to one or more mobile devices 141, 143. Guided activities comprise of multi-step descriptions of activities that a patient is interested in, that a doctor or medical practitioner might create and share/distribute. The content distribution module 137 distributes reports, results of tests, advisory information, technical papers, recipes, etc to individual users, to entire groups, etc. Textual guided activities are supported too, in addition to those that combine textual description, audio instructions, video instructions, graphics, and animation in multi-step tasks/activities.

The website 135 facilitates creating messages, questionnaires, uploading patient group lists, distributing messages and questionnaires, setting user profiles, reviewing messages, questionnaires, creating guided activities, distributing guided activities, assigning one or more patients, doctors, medical practitioners and others to various patient groups, expert panels, consulting groups, insurance groups, etc.

The patient group management server 111 receives an inquiry from one of the plurality of patients and shares it with at least one member of a patient group in which the one of the plurality of patients is a member. The patient group management server 111 enables communication of at least one of a response message, a coaching and guided activity, a questionnaire and relevant reference content by another member of the patient group in response to the inquiry.

In the health management system 105, patients are assigned to one or more patients groups, and they can interact with each other in the patient groups, send messages to each other, etc. Doctors, lab technicians, nurses, paramedics, hospice employees, chiropractors, physiotherapists, healthcare workers and insurance companies are also members of some patient groups. Ad hoc patient groups can be created as necessary. Membership is managed and closed groups are setup as necessary. Patient groups can be "managed groups" wherein one or more managers are assigned and they get messages from each of the non-manager members, which they can review and forward to the whole group, forward to other groups, or just respond back to. Non-manager members of a managed group communicate with the managers, and messages posted by the managers can be received by the whole group (or subset thereof as specified). And any member can respond to received messages, which goes to the managers first, where they can be processed, forwarded, responded back to, deleted, etc. Typically a doctor or a set of doctors are managers of patient groups that are of managed group type. In one embodiment, registered nurses and consultants working for doctors (who are managers) can also be included as managers by the doctors.

Peer-2-peer patient groups are also setup wherein any message posed is received by all members. In a peer-2-peer type group, any member can respond to received messages. Observer member types are also supported for such groups. The patient group management server 111 handles messages differently in how it distributes the messages within the group, based on the interaction type of a group (peer-2-peer or manage groups), based on a role for the sender in the group (manager, normal member, observer, etc.) and on other characteristics of the sender's profile and group characteristics.

In general, insurance company employees, other consulting doctors, and experts can be made members of these managed groups or peer-2-peer groups. In addition, observer members (who cannot post messages, but receive messages sent to the whole group, or those addressed specifically to them) are also be assigned. In one embodiment, in a group of patients where a doctor is a member of the group, an expert or specialist can be an observer. In a different embodiment, where a doctor is a manager of a patient group, the doctor is an observer in another specialist group composed of specialists in a field of medicine, and the doctor, as an observer, can forward a patient's inquiry to the manager of the specialist group, and receive a response back which he can share with the whole patient group (or send it back to the sender of the inquiry).

A user's group membership data is available at, and managed via, the patient group management server 111. In one embodiment, a user can download his group membership details (such as names and references of groups where the user is a member) into his mobile device 141, laptop/pc 117/ tablet. Subsequently, in interacting with the patient group management server 111, membership information is not accessed from the patient group management server 111, but locally accessed—this provides some efficiencies and speeds up user experience. Local membership information can be updated by the user.

In one embodiment, user access is managed via username/ password by the registration & login manager 127 of the patient group management server 111. In a related embodiment, validation of username/passwords provided by is user is first conducted in the user's device (his mobile device, laptop/pc/tablet), failing which it is conducted at the patient group management server 111. Specifically, a mobile client in the user's device (his mobile device, laptop/pc/tablet), facilitates such user access validation (using username/passwords for example) and user access to services provided by the health management system 105. In one embodiment, on successful login by a user using the mobile device 141 the first time with the patient group management server 111, the mobile device 141 receives a list of groups and group types that the user is currently a member of, and the mobile device 141 stores it locally in a file or database 121.

The health management system 105 supports creation and sending of an inquiry from a patient (or doctor or healthcare professional, etc.) wherein the inquiry is one of a query message in audio-assisted form, a questionnaire feedback, a remote patient data and an interest indicator survey input. One of the plurality of mobile devices of patients is communicatively coupled to the patient group management server 111. The inquiry typically originates on such a mobile device and the response to the inquiry is presented by the patient group management server 111 to the associated one of the plurality of patients via the mobile device. The response to the inquiry can also be sent to all the members of a patient group of which the inquiring patient is currently a member. Other members of a patient group are doctors, patient care personnel, healthcare practitioners, consultants, insurance company employees, etc.

Doctors can, in an adhoc manner, as needed, interact with their patients or patient groups. Thus, the patient group management server 111 makes doctor interactions efficient, timely, cost-effective. The doctors can use their mobile devices (cell phones, smartphones, tablets) and laptop/PC 117/computers to interact with the patient group management server 111. Specifically, the mobile devices 141, 143, 145, 147 of doctors and patients comprises a mobile client 153 that provides access to services provided by the patient group management server 111. Timely interaction with patients improves the quality of patient care. Information retrieved from patient premises makes it possible to efficiently and quickly diagnose a problem (for a remote patient) and provide necessary care and advice. Insurance companies can monitor and audit such activities and facilitate payment of doctors and other care givers/service providers, efficiently and cost-effectively The patient group management server 111 keeps tracks of all activities. It creates periodic records of patient care provided to individual patients by doctors, hospitals and other patient care providers. It provides detailed information on patient care provided, patient responses received from patients, coaching and guided activities provided to patients, etc. It makes reports on status of patient care, needs of patients, status of various problems that patients have reported, etc.

Messages from patients and from doctors are flagged by the patient as urgent, important, requests, etc. The message sender provides a message category, message type, and identifies any issues. In one embodiment, the message interaction module 123 provides appropriate functionality based on message category, message type, and identified issues for a message.

In one embodiment, users of the services provided by the health management system 105 include physicians, their nurses, physiotherapy personnel, case managers, and other healthcare providers that work at the same hospital, emergency center, urgent care center, clinic or practice. These users can interact with and send messages to each other, or to the whole group, or to multiple groups. They can form adhoc groups for communications if necessary. Messages sent to each other for interactions comprise of a text message (optional, as typing text is cumbersome on most mobile devices), voice recorded by user, digital photo taken, video recorded by user, etc. The patient group management server 111 manages the messages received, messages distributed, etc. It can provide lists of waiting messages to users. It can provide lists of questionnaires posted to the users, or provide lists of default questionnaires or patient status reports always available to all members of a group.

Other potential users of the health management system 105 of the current invention includes clinical trial companies, pharmaceutical companies, drug stores where a patient gets his/her medications, places where patients get lab tests conducted on blood, body fluids, etc, health care personnel in MRI centers and X-Ray centers, etc. A patient or a doctor can include such users into their patient groups temporarily or permanently. A patient or a doctor, for example, can ask these users questions and get answers.

In one embodiment, the patient group management server 111 is a managed hosted server in the cloud that is accessible over the Internet 113 from mobile device 141 and the pc/laptop 117.

The present invention provides support for alerts to patients, alerts to doctors, urgent messages to any user in a group, forwarding of messages from one group to another automatically based on patient alerts 9 factoring in alert types, alert categories, issue identified, etc).

In the health management system 105, the plurality of mobile devices each comprises a mobile client that interacts with the patient group management server 111. The mobile client 153 typically helps send an inquiry, displays the response message received for that inquiry, the coaching and guided activity received, the questionnaire received, and the relevant reference content received from the inquiry. The mobile client 153 integrates messaging with voice and digital photo, display of forms and questionnaires, presenting patient care coaching and other guided activities, and data collection from patient premises medical devices. The mobile client 153 validates user login locally in the mobile device first before initiating a remote login with the patient group management server.

Users of the plurality of mobile devices 141, 143, 145, 147 typically originate an inquiry and receive/peruse response to the inquiry. The response is either retrieved by or received by and subsequently presented by their corresponding mobile device or by more than one of the plurality of mobile devices. The response is received based on membership to the patient group, a group interaction type associated with the patient group and an inquiry type associated with the inquiry, for example.

The patient group management server 111 selectively communicates an inquiry from one of the plurality of patients to an external server communicatively coupled to the patient group management server 111, based at least on one of a patient profile, an inquiry type associated with the inquiry, and a patient group information. The patient group management server 111 receives a response to the inquiry from the external server (via the external server interface 139) and forwards the response to the inquiry to at least one of the plurality of mobile devices. It also receives followup responses from the plurality of mobile devices 141, 143, 145, 147 and forwards at least a portion of each of the followup responses to the external server. It also selectively forwards a billing transaction to the external server for processing.

In one embodiment, the patient group management server 111 selectively communicating an inquiry to an external server communicatively coupled to the patient group management server 111, based at least on one of a patient profile, an inquiry type associated with the inquiry and patient group information. It receives a response to the inquiry from the external server and forwards the response to at least one of the plurality of mobile devices 141, 143, 145, 147 associated with the patients in an associated patient group targeted by the external server for the response to the inquiry.

The patient group management server 111 receives a new message addressed to recipients from the external server. The recipients is a specific patient in a patient group, one or more patients from the patient group or the entire patient group, or a set of patient groups. The new message comprises at least one of text, audio, digital image and video components. The patient group management server 111 forwards the new message to the recipients specified.

The health management system 105 also comprises a website associated with the patient group management server 111 that facilitates creation of the inquiry by one of the plurality of patients employing a browser in a laptop 117, tablet or mobile device 141 communicatively coupled to the patient group management server. The website 135 communicates the response to inquiry to the browser wherein the website provides the content and the ability to simultaneously display a response message, a coaching and guided activity, a questionnaire, a relevant reference content and a data collection screen on the browser for perusal and access by the one of the plurality of patients.

FIG. 2 is a flow chart of an exemplary operation of the patient group management server 111 of the health management system 105. At a start block 205, the health management system is ready for access by users. At a next block 207, the patient group management server 111 that is communicatively coupled to a plurality of mobile devices of patients, receives an inquiry from one of the plurality of mobile devices. At a next block 209, it creates, a response to the inquiry comprising one or more of a message, a questionnaire for feedback, an interest inquiry form, a patient care related coaching instruction, a remote data collection command and a reference content. A message is a combination of an audio component, textual component, a graphic component, a video component, a digital photo component, and a reference to some patient data. At a next block 211, it sends the response to the inquiry to at least one of the plurality of mobile devices of patients.

Then at a next block 213, it gets a user followup response and processes it/stores it (locally in the mobile device, such as in a local file system or a local database/recordstore) and makes at least one appointment selectively based on the user followup response. The processing terminates at the end block 231.

In one embodiment, the exemplary operation also comprises the step of enabling a doctor to create a patient group among the plurality of patients, and providing an interface that makes it possible to send the same message, the same instructions or coaching to all the patients of a patient group, wherein the message, instructions or coaching comprise information on proper habits, diet, medications and patient care. It also comprises the step of verifying that the members of the patient group follow the instructions or coaching provided, and the additional step of sending reminders to the patient group, as necessary. Such reminders are for medications, therapy sessions, appointments made, etc. The exemplary operation also comprises the additional step of collecting data from patient premises devices for the patient group (the patient premises devices generate data that need to be remotely acquired and shared with doctors and labs instantaneously) and the step of sharing followup response from patients and data from patient premises devices with an external insurance company server as required.

In a different embodiment, the exemplary operation also comprises the step of facilitating creation of the inquiry by one of the plurality of patients employing a browser in a laptop, tablet or mobile device communicatively coupled to a website associated with, and managed by, the patient group management server 111. Additionally, it comprises the next step of conveying, by the website, the response to inquiry to the browser. The website provides the content and the ability to simultaneously display a response message, a coaching and guided activity, a questionnaire, a relevant reference content and a data collection screen on the browser for perusal and access by the one of the plurality of patients.

In yet another embodiment of the operation of the health management system, the patient group management server 111 provides a list of messages, a list of questionnaires, a list of coaching or guided activities or a list of data collection tasks currently waiting for the user one of the plurality of mobile devices. It also accepts user selection from the one of the plurality of mobile devices of an item listed in the list of messages, a list of questionnaires, a list of coaching or guided activities or a list of data collection tasks. It them facilitates retrieving the item selected and presenting the item selected to the one of the plurality of mobile devices.

FIG. 3 is a flow chart of an exemplary interaction by a mobile client in a mobile device with the patient group management server 111 in the health management system 105. At a start block 305, the operation starts when the mobile client is ready for use by a user (a patient or doctor, for example). At a next block 307, it prompts the user to login, and collects user login data before allowing the user to send inquiries, receive new messages or participate in a patient group. It then, at a next block 309, attempts to validate the user login data locally first in the mobile device before attempting a remote login validation.

After successful login by the user, at a next block 311 the mobile client sends an inquiry to the patient group management server 111 that is communicatively coupled to the mobile device, wherein the inquiry has a patient provided category, type, and issue identified. In general, different patient groups can have their own customized list of message categories, issues for each category, message types, etc.

At a next block 313 the mobile client receives from the patient group management server 111, in response to the inquiry, a response to the inquiry comprising one or more of an audio or video assisted message, a questionnaire for feedback, an interest inquiry form, a patient care related coaching instruction, a patient premises devices data collection command, and a reference content. The message is a combination of an audio component, textual component, a graphic component, a video component, a digital photo component, and a reference to some patient data.

At a next block 315 it displays the response to the inquiry for review by a user. The at a next block 317, it gathers a user input from the user. Then at a next block 319, it sends the user input as a user followup response if necessary. Later, at a next block 321, it gets at least one appointment selectively based on the user followup response and stores it.

At a next block 323, the mobile client receives data\over a Bluetooth communication link in the mobile device, a WiFi communication link (802.11b and all 802.11 variations) in the mobile device, or an USB communication link in the mobile device. The Bluetooth communication link, the WiFi communication link, and the USB communication link employ a Bluetooth circuitry, a WiFI circuitry and a USB circuitry, respectively, in the mobile device.

At a next block 325, the mobile client uploads the received data to the patient group management server or to an external server. Then at a next block 325, it selectively transfers data to another device in proximity, if necessary (or if requested by the user).

Finally the operation terminates at the end block 333.

In one embodiment, the mobile client displays all the components of the response to the inquiry simultaneously to the user. In another related embodiment, the mobile client displays the various components of the response to the inquiry in its own tabbed screen, wherein the response to the inquiry comprises one or more of the following components: an audio or video assisted message, a questionnaire for feedback, an interest inquiry form, a patient care related coaching instruction, a patient premises devices data collection command and a reference content. The message is usually a combination of an audio component, textual component, a graphic component, a video component, a digital photo component, and a reference to some patient data.

In another embodiment, the exemplary operation of the mobile client also includes the steps of showing a list of messages, a list of questionnaires, a list of coaching or guided activities or a list of data collection tasks currently waiting for the user of the mobile device, and accepting user selection of an item listed in the list of messages, a list of questionnaires, a list of coaching or guided activities or a list of data collection tasks. It also comprises the steps of retrieving the item selected and presenting the item selected to the user.

In a related embodiment, the operation of the mobile client requires the display of each of these lists in a separate tabbed section of a main screen of the mobile client. A user can select any of the presented tabs and review the associated list of items. For example, a messages tab displays a list of messages to select from (with message content displayed in a portion of the same screen, for example), a questionnaire tab displays a list of questionnaires, a coaching tab lists a set of pre-created guided activities and instructions for a doctor/nurse/medical practitioner/etc., a data collection tab provides buttons to initiate communication with other devices available locally (also referred to patient premises medical devices sometimes) with which the mobile client can interact with and retrieve data, send commands, etc.

As one of ordinary skill in the art will appreciate, the terms "operably coupled" and "communicatively coupled," as may be used herein, include direct coupling and indirect coupling via another component, element, circuit, or module where, for indirect coupling, the intervening component, element, circuit, or module does not modify the information of a signal but may adjust its current level, voltage level, and/or power level. As one of ordinary skill in the art will also appreciate, inferred coupling (i.e., where one element is coupled to another element by inference) includes direct and indirect coupling between two elements in the same manner as "operably coupled" and "communicatively coupled."

Although the present invention has been described above in terms of funds transfer and banking operations, the present invention is not limited to such embodiments. It will be obvious to one of average skill in the art that various other human activities, such as mail delivery services, package delivery services, document delivery services can adopt this invention to solve similar or related problems.

The present invention has also been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claimed invention.

The present invention has been described above with the aid of functional building blocks illustrating the performance of certain significant functions. The boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention.

One of average skill in the art will also recognize that the functional building blocks, and other illustrative blocks, modules and components herein, can be implemented as illustrated or by discrete components, application specific integrated circuits, processors executing appropriate software and the like or any combination thereof.

Moreover, although described in detail for purposes of clarity and understanding by way of the aforementioned embodiments, the present invention is not limited to such embodiments. It will be obvious to one of average skill in the art that various changes and modifications may be practiced within the spirit and scope of the invention, as limited only by the scope of the appended claims.

What is claimed is:

1. A health management system that facilitates interaction with a plurality of patients, the health management system comprising:

a patient group management server that is communicatively coupled to a plurality of mobile devices of patients, the patient group management server comprising:
- a message interaction module configured to manage message based interactions between patients and other members within each of a plurality of patient groups;
- a questionnaire distribution and feedback collection module configured to distribute questionnaires and collect data and feedback;
- a remote patient premises data collection module configured to collect data from medical devices employed at a remote patient premises;
- a coaching distribution module configured to distribute guided activities regarding proper habits, diet, medications, patient care, information a patient is interested in, and activities that a doctor or medical practitioner has created; and
- a content distribution service module configured to distribute technical papers, recipes, relevant reference content, advisory information, reports and results of tests to the patients;

the patient group management server configured to receive an inquiry from one of the plurality of patients via a corresponding one of the plurality of mobile devices and share it with at least another member of a patient group among the plurality of the patient groups in which the one of the plurality of patients is a member;

the patient group management server configured to receive and share a response message, a coaching and guided activity, a questionnaire and a relevant reference content communicated by the at least another member of the patient group in response to the inquiry; and the patient group management server configured to share a followup response from the one of the plurality of patients with an external insurance company server, as required.

2. The health management system of claim 1 wherein the inquiry is one of a query message in audio-assisted form, a questionnaire, feedback, a remote patient data and an interest indicator survey input.

3. The health management system of claim 2 further comprising:
the patient group management server configured to selectively communicate an inquiry from one of the plurality of patients to an external server communicatively coupled to the patient group management server, based at least on one of a patient profile, an inquiry type associated with the inquiry, and a patient group information;
the patient group management server configured to receive a response to the inquiry from the external server and to forward the response to the inquiry to at least one of the plurality of mobile devices;
the patient group management server configured to receive followup responses from the at least one of the plurality of mobile devices and to forward at least a portion of each of the followup responses to the external server; and
the patient group management server configured to selectively forward a billing transaction to the external server for processing.

4. The health management system of claim 2 further comprising:
the patient group management server configured to selectively communicate an inquiry to an external server communicatively coupled to the patient group management server, based at least on one of a patient profile, an inquiry type associated with the inquiry, and a patient group information; and
the patient group management server configured to receive a response to the inquiry from the external server and forwards the response to at least one of the plurality of mobile devices associated with the patients in an associated patient group targeted by the external server for the response to the inquiry.

5. The health management system of claim 2 further comprising:
the patient group management server configured to receive a new message addressed to recipients in one of the plurality of patient groups from an external server, wherein the recipients are:
- a specific patient in a specific patient group among the plurality of patient groups,
- one or more patients from the specific patient group or the entire membership of the specific patient group, or
- a set comprising one or more patient groups of the plurality of patient groups, wherein the new message comprises at least one of text, audio, digital image and video components; and
the patient group management server forwards the new message to the recipients specified.

6. The health management system of claim 2 further comprising:
a website associated with the patient group management server configured to facilitate creation of the inquiry by one of the plurality of patients employing a browser in a laptop, tablet or mobile device communicatively coupled to the patient group management server; and
the website configured to communicate the response to inquiry to the browser wherein the website provides the content and the ability to simultaneously display a response message, a coaching and guided activity, a questionnaire, a relevant reference content and a data collection screen on the browser for perusal and access by the one of the plurality of patients.

7. The health management system of claim 1 further comprising:
the one of the plurality of mobile devices of patients being communicatively coupled to the patient group management server and originating the inquiry that is shared by the patient group management server with one of a plurality of patient groups; and
the patient group management server configured to receives responses to the inquiry from one or more members of the one of a plurality of patient groups and to communicate the responses to the one of the plurality of mobile devices for review by the associated one of the plurality of patients.

8. The health management system of claim 1 wherein the one of the plurality of mobile devices comprises a mobile client configured to interacts with the patient group management server and display the response message, the coaching and guided activity, the questionnaire and the relevant reference content;
the mobile client also configured to integrates messaging with voice and digital photo, display of forms and questionnaires, presenting patient care coaching and other guided activities, and data collection from patient premises medical devices; and
the mobile client configured to validates user login locally in the one of the plurality of mobile devices first, before initiating a remote login with the patient group management server.

9. The health management system of claim 1 further comprising:
one of the plurality of mobile devices originating the inquiry wherein the response to the inquiry is either retrieved by or received by, and subsequently presented by, the one of the plurality of mobile devices, or by more than one of the plurality of mobile devices based on:
membership to the plurality of patient groups;
a group interaction type associated with each of the plurality of patient groups; and
an inquiry type associated with the inquiry.

10. A method of operating a health management system by a patient group management server that facilitates interaction with a plurality of patients, the method comprising:
providing, by the patient group management server, an interface that makes it possible to send same message, same instructions or coaching to the plurality of patients, wherein the same message, the same instructions or the coaching comprise information on proper habits, diet, medications and patient care:
receiving and sharing, by the patient group management server that is communicatively coupled to a plurality of mobile devices of patients, an inquiry from one of the plurality of mobile devices;
gathering by the patient group management server, a response to the inquiry created by one of the patients employing a second one of a plurality of mobile devices, the response to the inquiry selectively comprising:
a message, wherein the message is a combination of an audio component, textual component, a graphic component, a video component, a digital photo component, and a reference to patient data;
a questionnaire for feedback;
an interest inquiry form;
a patient care related coaching instruction;
a remote data collection command; and
a reference content;
sending by the patient group management server, the response to the inquiry to at least one of the plurality of mobile devices of patients;
getting, by the patient group management server, a user followup response and storing it;
sharing, by the patient group management server, the followup response from patients with an external insurance company server, as required; and
making, by the patient group management server, at least one appointment selectively based on the user followup response.

11. The method of claim 10 further comprising:
enabling, by the patient group management server, a doctor to create a patient group among the plurality of patients;
providing, by the patient group management server an interface that makes it possible to send the same message, the same instructions or coaching to the patient group, wherein the message, instructions or coaching comprise information on proper habits, diet, medications and patient care;
verifying, by the patient group management server that the members of the patient group follow the instructions or coaching;
sending, by the patient group management server, reminders to the patient group;
collecting data from patient premises devices for the patient group, by the patient group management server, wherein the patient premises devices generate data that need to be remotely acquired and shared with doctors and labs instantaneously; and
sharing, by the patient group management server followup response from patients and data from patient premises devices with an external insurance company server as required.

12. The method of claim 10 further comprising:
facilitating, by the patient group management server, creation of the inquiry by one of the plurality of patients employing a browser in a laptop, tablet or mobile device communicatively coupled to a website associated with, and managed by, the patient group management server; and
conveying, by the website, the response to the inquiry to the browser wherein the website provides the content and the ability to simultaneously display a response message, a coaching and guided activity, a questionnaire, a relevant reference content and a data collection screen on the browser for perusal and access by the one of the plurality of patients.

13. The method of claim 10 further comprising:
providing, by the patient group management server, a list of messages, a list of questionnaires, a list of coaching or guided activities or a list of data collection tasks currently waiting for a user of one of the plurality of mobile devices;
accepting, by the patient group management server, a user selection made by the user from the one of the plurality of mobile devices, the user selection comprising an item listed in one of the list of messages, the list of questionnaires, the list of coaching or guided activities or the list of data collection tasks;
and
presenting, by the patient group management server, the item selected to the one of the plurality of mobile devices.

14. A method of interacting with a health management system by a mobile client in a mobile device, the method comprising:
sending an inquiry to a patient group management server that is communicatively coupled to the mobile device, wherein the inquiry has a patient provided category, type, and issue identified;
receiving, a response to the inquiry, from the patient group management server, the response to the inquiry selectively comprising:
an audio or video assisted message wherein the message is a combination of an audio component, textual component, a graphic component, a video component, a digital photo component, and a reference to patient data;
a questionnaire for feedback;
an interest inquiry form;
a patient care related coaching instruction;
a patient premises devices data collection command; and
a reference content;
displaying the response to the inquiry for review by a user;
gathering a user input from the user;
sending the user input as a user followup response,
getting at least one appointment based on the user followup response and storing it; and
sharing the followup response with an external insurance company server, as required.

15. The method of claim 14 further comprising:
prompting the user to login, and collecting user login data, before allowing the user to send inquiries, receive new messages or participate in a patient group; and attempting to validate the user login data locally first in the mobile device before attempting a remote login validation.

16. The method of claim 15 further comprising:

receiving data by the mobile client over a Bluetooth communication link in the mobile device, a WiFi communication link in the mobile device, or an USB communication link in the mobile device, wherein the Bluetooth communication link, the WiFi communication link, and the USB communication link employ a Bluetooth circuitry, a WiFi circuitry and a USB circuitry, respectively, in the mobile device;

uploading the received data to the patient group management server or to an external server; and selectively transferring the received data to another device in proximity.

17. The method of claim 14 wherein the mobile client displays all the components of each response to the inquiry simultaneously to the user.

18. The method of claim 14 wherein the mobile client displays the various components of each response to the inquiry in its own tabbed screen, wherein each response to the inquiry selectively comprises the following components:

an audio or video assisted message wherein the message is a combination of an audio component, textual component, a graphic component, a video component, a digital photo component, and a reference to some patient data;

a questionnaire for feedback;

an interest inquiry form;

a patient care related coaching instruction;

a patient premises devices data collection command; and a reference content.

19. The method of claim 18 further comprising:

showing a list of messages, a list of questionnaires, a list of coaching or guided activities or a list of data collection tasks currently waiting for the user of the mobile device;

accepting user selection of an item listed in the list of messages, a list of questionnaires, a list of coaching or guided activities or a list of data collection tasks;

retrieving the item selected; and presenting the item selected to the user.

20. The method of claim 19 wherein each of these lists is displayed in a separate tabbed section of a main screen.

* * * * *